United States Patent
Kruk et al.

(12)

(10) Patent No.: US 6,479,697 B2
(45) Date of Patent: Nov. 12, 2002

(54) PROCESS FOR THE PREPARATION OF α-(2-4-DISULFOPHENYL)-N-TERT-BURTYLNITRONE AND PHARMACEUTICALLY ACCEPTABLE SALTS THEREOF

(75) Inventors: Henry Kruk, San José, CA (US); John McGinley, San Francisco, CA (US); Sergei Pouhov, Fremont, CA (US); John Vajda, Sunnyvale, CA (US); Jörgen Blixt, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/806,832

(22) PCT Filed: Jan. 4, 2001

(86) PCT No.: PCT/SE01/00007

§ 371 (c)(1),
(2), (4) Date: Apr. 5, 2001

(87) PCT Pub. No.: WO01/51460

PCT Pub. Date: Jul. 19, 2001

(65) Prior Publication Data

US 2002/0128318 A1 Sep. 12, 2002

(30) Foreign Application Priority Data

Jan. 10, 2000 (SE) .............................................. 0000055

(51) Int. Cl.[7] .................... C07C 309/00; C07C 211/00; C07C 239/00
(52) U.S. Cl. .................... 562/84; 564/282; 564/300; 564/396

(58) Field of Search ................................. 564/282, 300, 564/396; 568/30, 77; 562/84

(56) References Cited

U.S. PATENT DOCUMENTS 5,475,032 A * 12/1995 Carney

FOREIGN PATENT DOCUMENTS

| FR | 1437188 | 3/1966 |
| WO | WO 95/17876 | 7/1995 |
| WO | WO 00/02848 | 1/2000 |

OTHER PUBLICATIONS

Janzen et al. " Spin Trapping Chemistry Of Sodium 2–Sulfonatophenyl t–Butyl Nitrone". Tetrahedron Letters No. 35 1979; pp 3229–3232.*

Janzen et al; "Spin Trapping Chemistry of Sodium 2–Sulfonatophenyl t–Butyl Nitrone (Na+2–SPBN–). A Negatively Charged Water–Soluble SpinTrap"; Tetrahedron Letters, vol. 35, p. 3229, p. 3232; 1979.

Hinton et al; "Synthesis and Characterization of Phenyl–Substituted C–Phenyl–N–tert–butylnitrones and Some of Their Radical Adducts"; J. Org. Chem., vol. 57, No. 9, p. 2646 –p. 2651; p. 2648, left column, 1992.

* cited by examiner

Primary Examiner—Sreeni Padmanabhan
Assistant Examiner—Sikarl A. Witherspoon
(74) Attorney, Agent, or Firm—Nixon & Vanderhye

(57) ABSTRACT

A process for the preparation of α-(2,4-disulfophenyl)-N-tert-butylnitrone diacids and pharmaceutically acceptable salts thereof by the reaction of the corresponding disulfophenyl aldehyde with N-tert-butylhydroxylammonium acetate is disclosed.

10 Claims, No Drawings

PROCESS FOR THE PREPARATION OF α-(2-4-DISULFOPHENYL)-N-TERT-BURTYLNITRONE AND PHARMACEUTICALLY ACCEPTABLE SALTS THEREOF

This application is a 371 of PCT/SE01/00007 filed Jan. 4, 2001, now WO 01/51460 published Jul. 19, 2001.

FIELD OF THE INVENTION

This invention relates to a novel process for the preparation of α(2,4-disulfophenyl)-N-tert-butylnitrone and pharmaceutically acceptable salts thereof. These compounds have previously been disclosed as being useful as medicaments. Such compounds are alternatively named as 4-[(tert-butylimino)methyl]benzene-1,3-disulfonic acid N-oxide derivatives.

BACKGROUND OF THE INVENTION

U.S. Pat. No. 5,488,145 discloses α-(2,4-disulfophenyl)-N-tert-butylnitrone, pharmaceutically acceptable salts thereof and related pharmaceutical compositions. U.S. Pat. No. 5,475,032 discloses the use of such compositions in the treatment of stroke and of progressive central nervous system function loss conditions. U.S. Pat. No. 5,508,305 discloses the use of such compositions for ameliorating the side effects caused by oxidative damage resulting from antineoplastic disease treatment. Similar disclosures are also made in WO 95/17876. U.S. Pat. No. 5,780,510 discloses the use of these same compounds in the treatment of concussion.

Various methods are available for the synthesis of nitrones. The most often used method involves the usually uncatalysed condensation reaction of a hydroxylamine derivative with an aldehyde or ketone (J. S. Roberts in D. H. R. Barton and W. D. Ollis, *Comprehensive Organic Chemistry*, Volume 2, pp. 500–504, Pergamon Press, 1979; R. D. Hinton and E. G. Janzen, *J. Org. Chem.*, 1992, 57, pp. 2646–2651). The utility of this reaction is impaired by its susceptibility to steric hindrance, slow reaction rates, and, in certain cases, by the relative inaccessibility and/or instability of the hydroxylamine starting material. The latter problems can sometimes be overcome by in situ generation of the required hydroxylamine by reduction of a more readily available compound such as the corresponding nitro derivative. This general methodology is employed in the above-described patents where the preparation of α(2,4-disulfophenyl)-N-tert-butylnitrone is described as involving the reaction of 4-formyl-1,3-benzenesulfonic acid with N-tert-butylhydroxylamine in refluxing methanol for approximately 18 hours.

α-(2-Sulfophenyl)-N-tert-butylnitrone has been prepared by reaction of 2-formylbenzenesulfonic acid sodium salt with N-tert-butylhydroxylamine in refluxing ethanol for 2 days (E. G. Janzen and R. V. Shetty, *Tetrahedron Letters*, 1979, pages 3229 to 3232).

A modification of this type of methodology for the manufacture α-phenyl-N-methylnitrone has been described in French Patent 1,437,188 to E.I. DuPont de Nemours and Co.

We now disclose a novel process that possesses significant advantages for the preparation of α-(2,4-disulfophenyl)-N-tert-butylnitrone and salts thereof and is also particularly suited to large-scale production.

DISCLOSURE OF THE INVENTION

In one aspect, this invention provides a process for the preparation of a compound of general formula (I)

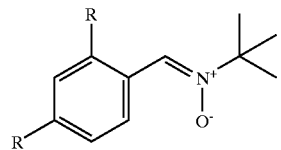

wherein each R independently represents $SO_3H$ or a salt thereof.

This process involves reaction of an aldehyde of general formula (II)

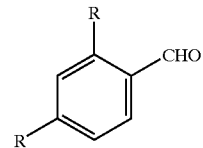

wherein R is as defined above, with N-tert-butylhydroxylammonium acetate (III)

$(CH_3)_3CNHOH \cdot CH_3CO_2H$  (III)

In a second aspect, this invention provides a method for preparing and recovering a compound of general formula (I). In the first step of this process, the compound is prepared as just described. In a subsequent step, the compound is isolated.

DETAILED DESCRIPTION OF THE INVENTION

Products and Starting Materials

In this process, an aldehyde of general formula (II) is reacted with N-tert-butylhydroxylammonium acetate to form an α-(2,4-disulfophenyl)-N-tert-butylnitrone compound of general formula (I). The compounds of general formulae (I) and (II) may be acids or they may be salts.

Salts of compounds of formula (1) above may be formed by reacting the free acid (wherein R represents $SO_3H$), or another salt thereof, with two or more equivalents of an appropriate base, using methods that are well known in the art.

The salts of compounds of formulae (I) and (II) referred to above will normally be those formed with pharmaceutically acceptable cations. The cation may be a monovalent material such as sodium, potassium, lithium, ammonium, alkylammonium or diethanolammonium. Alternatively, it may be a polyvalent cation such as calcium, magnesium, aluminium or zinc. It may also be a mixed salt formed with a polyvalent cation such as calcium or magnesium in combination with a pharmaceutically acceptable anion such as halide (for example chloride), phosphate, sulphate, acetate, citrate or tartrate.

The two R's in these formulae are usually the same. However, they can be independently selected from the possibilities just enumerated.

It is preferred that the two R's in formulae (I) and (II) above be the same and each represents $SO_3^-Na^+$.

N-tert-Butylhydroxylammonium acetate is disclosed in co-pending PCT patent application WO 00/02848.

The aldehydes of general formula (II) are either commercially available or may be prepared from commercially available materials using methods that are well known in the art. Commercial 4-formyl-1,3-benzenedisulfonic acid disodium salt (II; R=$SO_3^-Na^+$) typically contains small but significant amounts of the corresponding benzyl alcohol and the corresponding benzoic acid derivatives and of sodium chloride as impurities. It is preferable, but not essential, that such material is purified before use in the process of the present invention. 4-Formyl-1,3-benzenedisulfonic acid disodium salt (II; R=$SO_3^-Na^+$) is typically associated with varying amounts of water. The proportion of such water generally is not critical to the process of the present invention but generally may be taken into account when determining the overall composition of the compound (I)-forming reaction mixture.

The Process

The first step is the condensation of the N-tert-butylhydroxylammonium acetate (III) with the aldehyde (II). This reaction is typically conducted in a batch mode with agitation. It could, if desired, be carried out continuously in a flow reaction system.

In this process it is preferred that in general about 1.25 to 2.5 equivalents of N-tert-butylhydroxylammonium acetate (III) is used for each equivalent of the aldehyde (II). It is particularly preferred that about 1.6 to 2.0 equivalents of N-tert-butylhydroxylammonium acetate (III) is used.

The condensation of the present invention is carried out in solution, using a suitable inert solvent in which the starting materials are sufficiently soluble. It is preferred that a suitable polar organic solvent such as an alcohol, or mixture of alcohols, is used as solvent. It is particularly preferred that the solvent is methanol. It is further preferred that the reaction mixture contains a suitable percentage of water, generally less than 10% by volume, such as from about 2% to 10% by volume. It is particularly preferred that the solvent contains about 5% by volume of water. It has been found that the presence of a suitable amount of water provides significant advantages, particularly with regards to inhibiting the conversion of the aldehyde (II) into the undesirable acetal side product (IV)

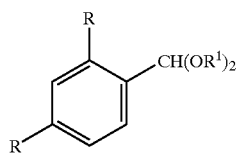

(IV)

by reaction with the solvent $R^1OH$.

The presence of a suitable amount of water in the solvent also increases the solubility of the 4-formyl-1,3-benzenedisulfonic acid disodium salt (II; R=$SO_3^-Na^+$) starting material and thereby significantly improves the kinetics of the process and enables the use of a more concentrated system.

The proportion of reaction solvent is typically maintained at about 2 to 8 mL of solvent per gram of nitrone product or greater, with proportions of from 2 to 6 and especially 3 to 4 mL/g being preferred.

The condensation is conducted at a temperature from about ambient temperature to about 150° C., good results being achieved at temperatures of from about ambient to about 125° C., with temperatures of from about 40° C. to about 100° C. being preferred.

The condensation reaction is relatively facile and is typically essentially complete in from about 15 minutes to about 5 hours with reaction time of from 30 to 90 minutes being typical. In practice, the degree of reaction is monitored analytically and the reaction is continued until a suitable degree of reaction is achieved.

The isolation of the product of formula (I) formed in the above condensation may be achieved by using standard techniques that are well known in the art. It is particularly advantageous that the product be isolated using a suitable crystallisation technique. Thus in a typical isolation, on completion of the reaction of the aldehyde (II) with N-tert-butylhydroxylammonium acetate (III), the reaction mixture is cooled to ambient temperature and then filtered in order to remove any insoluble material. The filtrate is then adjusted to a temperature that may be from 0° C. up to the reflux temperature of the solvent, but is preferably from 35 to 50° C., and crystallisation is induced by the addition of a suitable crystallisation agent such as isopropanol or ethyl acetate. The optimal precipitation temperature may vary depending on the scale of the reaction, on whether the suspension is stirred or allowed to stand, and on the desired particle size of the solid product.

The crystallisation agent is typically an organic liquid that is miscible with the reaction solvent but one in which the nitrone product is less soluble. The agent is also generally a volatile material, such as a material having 5 or less carbon atoms. The solid product is isolated by filtration and dried. The use of isopropanol, as a crystallisation agent, is particularly preferred.

Alternatively, crystallisation may be induced by the addition of a suitable agent such as isopropanol or ethyl acetate without the filtrate having first been heated. Again, the use of isopropanol is particularly preferred.

The water content of α-(2,4-disulfophenyl)-N-tert-butylnitrone disodium salt obtained using the process of the present invention is dependent on the nature of the methodology used for the isolation of the product and the final drying process that is used. Thus, extensive drying at elevated temperatures and under reduced pressure will yield essentially anhydrous material. Such material is however significantly hygroscopic, forming eventually a trihydrate. Drying of the trihydrate regenerates the anhydrous form. The trihydrate form is obtained directly by crystallisation of α-(2,4-disulfophenyl)-N-tert-butylnitrone disodium salt from hot water, or by passing humidified air over the solid.

Addition of up to about 5% volume of water to the crystallisation agent can push the product toward the hydrated form and decrease the amount of occluded organic liquids in the crystalline product and can lower impurity levels such as the level of unreacted aldehyde.

The invention is illustrated, but in no way limited, by the following examples.

EXAMPLE 1

α-(2.4-Disulfophenyl)-N-tert-butylnitrone disodium salt (10 g scale)

4-Formyl-1,3-benzenedisulfonic acid disodium salt (10.0 g, 27.6 mmol, 85.6% w/w), N-tert-butylhydroxylammonium acetate (6.1 g, 37.5 mmol, 1.4 equiv., 91.6% w/w), water (2 g) and methanol (38 g) were added to a 100 mL three-necked bottle at room temperature under an atmosphere of nitrogen gas. The mixture was stirred and the bottle was lowered into an oil bath maintained at 72° C. After 2.3 h, HPLC analysis (% area) showed that <0.3 area% of 4-formyl-1,3-benzenedisulfonic acid disodium salt remained. The clear filtrate was cooled to 20° C. and filtered. The clear solution was transferred to a 250 mL bottle, heated to reflux, and then isopropanol (70 g) was added dropwise. Crystal growth began when isopropanol (40 g) had been added. The hot bath was replaced with a cool water bath and the slurry was cooled to 11° C. After 30 minutes the product was isolated by filtration and sucked dry giving a white solid (11.2 g). This material was dried at 50° C. in a vacuum oven overnight. The isolated, dried weight was 8.55 g (78.8%).

Chromatographic purity (area% HPLC) showed greater than 99%
α-(2,4-disulfophenyl)-N-tert-butylnitrone disodium salt.

EXAMPLE 2

α-(2,4-Disulfophenyl)-N-tert-butylnitrone disodium salt (100 g scale)

4-Formyl-1,3-benzenedisulfonic acid disodium salt (100.0 g, 0.31 mol, 96.3% w/w), N-tert-butylhydroxylammonium acetate (66.8 g, 0.43 mol, 1.4 equiv., 97.0% w/w), water (10 g) and methanol (337 mL) were added to a 1 L jacketed three-necked flask at ambient temperature. The mixture was stirred and heated at 72° C. After 3 h, HPLC analysis showed that <0.2 area% of 4-formyl-1,3-benzenedisulfonic acid disodium salt was present. The reaction mixture was cooled and filtered. The filtrate was transferred to a 2 L reflux apparatus and heated to 80° C. When the mixture had come to reflux, isopropanol (765 mL) was added dropwise, and reflux was continued for a further 0.5 h. The resulting suspension was cooled to below 11° C. The white solid was filtered off and dried in a vacuum oven for 24 h at 50° C. Yield 83.0 g (72.8%).

Chromatographic purity (area% HPLC) showed greater than 99%
α-(2,4-disulfophenyl)-N-tert-butylnitrone disodium salt.

EXAMPLE 3

α-(2,4-Disulfophenyl)-N-tert-butylnitrone disodium salt (500 g scale)

4-Formyl-1,3-benzenedisulfonic acid disodium salt (500.0 g, 1.4 mol, 87.0% w/w), N-tert-butylhydroxylammonium acetate (336.0 g, 2.18 mol, 1.5 equiv., 97.0% w/w), water (20 g) and methanol (1700 mL) were added to a 5L jacketed three-necked flask, fitted with an overhead stirrer and recirculating heating bath, at room temperature. The mixture was stirred and the flask heated at 72° C. After 3.0 h, the solution was filtered. The filtrate was then heated to 80° C. and refluxed for 1 hour. Solvent (760 mL) was then removed by distillation at atmospheric pressure. Isopropanol (2200 mL) was then added and the suspension cooled to <11° C., filtered and dried in a vacuum oven for 96 h to yield the product as a white solid.

Chromatographic purity (area% HPLC) showed greater than 99%
α-(2,4-disulfophenyl)-N-tert-butylnitrone disodium salt.

EXAMPLE 4

α-(2,4-Disulfophenyl)-N-tert-butylnitrone disodium salt (750 g scale)

4-Formyl-1,3-benzenedisulfonic acid disodium salt (750.0 g, 2.32 mol, 85.6% w/w), N-tert-butylhydroxylammonium acetate (501.0 g, 3.26 mol, 1.4 equiv., 91.6% w/w), water (150 g) and methanol (2530 mL) were added to a 5 L jacketed three-necked flask at ambient temperature. The mixture was stirred and heated at 72° C. After 3.2 h, HPLC analysis showed that <0.2 area% of 4-formyl-1,3-benzenedisulfonic acid disodium salt remained. The reaction mixture was filtered through an in line filter. The filtrate was transferred to a distillation apparatus and the solution was then heated to 80° C. Isopropanol (1000 mL) was then added and distillation was started. A second portion of isopropanol (1000 mL) was added and distillation was continued until the distillate temperature reached 80° C. The resulting suspension was cooled to below 11° C., filtered, and the solid obtained was dried for 2 h to give the product as a white solid. Yield was 744.5 g (80.7%).

Chromatographic purity (area% HPLC) showed greater than 99%
α-(2,4-disulfophenyl)-N-tert-butylnitrone disodium salt.

EXAMPLE 5

α-(2,4-Disulfophenyl)-N-tert-butylnitrone disodium salt (100 g scale)

4-Formyl-1,3-benzenedisulfonic acid disodium salt (100.0 g, 0.31 mol, 96.3% w/w), N-tert-butylhydroxylammonium acetate (66.8 g, 0.43 mol, 1.4 equiv., 97.0% w/w), water (20 g) and methanol (337 mL) were added to a 1 L three-necked flask fitted with a heating mantle, at room temperature. The mixture was stirred and heated to 72° C. The reaction mixture was cooled to room temperature. Sodium methoxide (3.5 g, 64.7 mmol) was then added and the mixture was stirred for 0.5 h. The mixture was then filtered. HPLC analysis showed that <0.2 area% of 4-formyl-1,3-benzenedisulfonic acid disodium salt remained in the filtrate. The reaction mixture was transferred to a 1 L distillation apparatus and the solution was then heated to 80° C. After 100 mL of distillate had been collected, isopropanol (400 mL) was added and distillation was continued until the distillate temperature reached 78° C. The resulting suspension was filtered at 60° C. and the solid obtained was dried in a vacuum oven for 24 h to give the product as a white solid. Yield was 91.1 g (82.8%).

Chromatographic purity (area% HPLC) showed greater than 99%
α-(2,4-disulfophenyl)-N-tert-butylnitrone disodium salt.

EXAMPLE 6

α-(2,4-Disulfophenyl)-N-tert-butylnitrone disodium salt (without water addition) (100 g scale)

4-Formyl-1,3-benzenedisulfonic acid disodium salt (100.0 g, 0.32 mol, 99.6% w/w) was added to a 1 L round bottom flask fitted with a magnetic stirring bar and heating mantle. Methanol (400 mL) and N-tert-butylhydroxylammonium acetate (73.9 g, 0.48 mol, 1.5 equiv., 97.0% w/w) were added sequentially. The mixture was stirred and heated under reflux. After 6 h, HPLC analysis showed 99.1 area % of
α-(2,4-disulfophenyl)-N-tert-butylnitrone. The reaction mixture was a white suspension. Isopropanol (800 mL) was then added and the suspension was cooled to 2° C. The product was filtered off using a Buchner funnel, rinsed with isopropanol (200 mL) and then dried in a vacuum oven at 50° C. for 7 h. Yield was 88.0 g (71.9%). This example demonstrates that the condensation can be conducted without adding water to the reaction mixture.

EXAMPLE 7

α-(2,4-Disulfophenyl)-N-tert-butylnitrone disodium salt (4600 g scale)

4-Formyl-1,3-benzenedisulfonic acid disodium salt (4590.9 g, 14.3 mol, 98.1% w/w), N-tert-butylhydroxylammonium acetate (3988.4 g, 24.6 mol, 98.0% w/w), water (760 mL) and methanol (12.6 L) were stirred and heated in a 50 L reactor with a jacket temperature of 75° C. After 60 min reflux, HPLC (% area) analysis showed that the reaction was complete (<0.3% of 4-formyl-1,3-benzenedisulfonic acid disodium salt remained). The hot clear solution was transferred through an in-line filter to a second 50 L reactor, preheated at 75° C. After a further 30 minute reflux, isopropanol (30.0 L) was added at a rate of 1.2 L/minute. The reaction mixture was cooled to <30° C., filtered, washed with isopropanol (2×8 L) then dried in a Gruenberg oven at 70° C. for 47 hours, to give the product as a white solid. Yield was 81%.

EXAMPLE 8

α-(2,4-Disulfophenyl)-N-tert-butylnitrone disodium salt (4600 g scale)

4-Formyl-1,3-benzenedisulfonic acid disodium salt (4598.9 g, 14.4 mol, 98.0% w/w), N-tert-butylhydroxylammonium acetate (4000.0 g, 24.6 mol, 98.0% w/w), water (750 mL) and methanol (12.6 L) were stirred and heated in a 50 L reactor with a jacket temperature of 75° C. After 30 minutes reflux, HPLC (% area) analysis showed that the reaction was complete (<0.3% of 4-formyl-1,3-benzenedisulfonic acid disodium salt remained). The hot clear solution was transferred through an in-line filter to a second 50 L reactor, preheated at 75° C. After 15 minutes further reflux, the reactor was cooled to 45° C. and isopropanol (30.0 L) was added at a rate of 1.2 L/min. The reaction was cooled to 19° C. and water (1400 mL) was added. The suspension was allowed to stand for 18 hours. It was then filtered and the solid washed with isopropanol (2×8 L). The product was dried in a Gruenberg oven at 85° C. for 23 hours, to give the product as a white solid. Yield was 76%.

EXAMPLE 9

α-(2,4-Disulfophenyl)-N-tert-butylnitrone disodium salt (43 kg scale)

4-Formyl-1,3-benzenedisulfonic acid disodium salt (45 kg) was added as a solid to a 500 L reactor containing stirred N-tert-butylhydroxylammonium acetate (39 kg) in water (8.6 L) and methanol (111 kg) under an inert (nitrogen) atmosphere. The mixture was stirred and heated with a jacket temperature of 70° C. After the internal temperature reached 60° C., heating was continued for an additional 2 to 18 hours. The reaction was deemed to be complete when HPLC (% area) analysis showed <0.3% of 4-formyl-1,3-benzenedisulfonic acid disodium salt remained. The hot clear solution was then in-line filtered while being transferred to a second 500 L reactor, preheated at 35° C. Isopropanol (267 kg) was added to precipitate the product. Water (13.5 L) was then added and the mixture was allowed to stand for 12 to 18 hours. The white suspension was transferred to a filter dryer, washed with isopropanol (2×71 kg), then dried under vacuum (with a slight nitrogen flow) with a jacket temperature of 80° C., to give the product as a white solid (43 kg).

The surprising finding that the aldehyde of general formula (II) can be reacted directly with N-tert-butylhydroxylammonium acetate is particularly advantageous. The free base form of N-tert-butylhydroxylamine is unstable, tending in particular to undergo aerial oxidation. This is evidenced by the formation of blue colours which indicate the presence of the oxidation product, 2-methyl-2-nitrosopropane. The free base of N-tert-butylhydroxylamine cannot therefore easily be stored as such but must be freshly generated immediately before use on each and every occasion that it is required. This is a potential disadvantage of processes that might require handling of N-tert-butylhydroxylamine as the free base. This disadvantage becomes particularly troublesome when reactions are conducted on a large scale. The direct use of the acetate salt of N-tert-butylhydroxylamine in the process of the present invention provides a solution to this problem. Furthermore, if other salts such as N-tert-butylhydroxylammonium chloride are be substituted for N-tert-butylhydroxylammonium acetate in the above process, the reaction fails to work satisfactorily.

Not only can N-tert-butylhydroxylammonium acetate be used directly in the present invention, but also the reaction with the aldehyde of formula (II) proceeds considerably faster than when N-tert-butylhydroxylamine free base is used. Thus, in the present process, the reaction is typically complete within 1.5 hours, even on a 5000 g scale.

What is claimed is:

1. A process for the preparation of a compound of general formula (I)

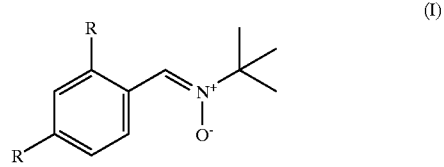

wherein each R independently represents $SO_3H$ or a salt thereof, which process involves reaction of an aldehyde of general formula (II)

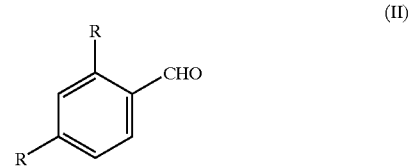

wherein R is as defined above, with N-tert-butylhydroxylammonium acetate in a liquid reaction solvent.

2. A process according to claim 1 wherein R represents $SO_3^-Na^+$.

3. A process according to claim 1 wherein 1.25 to 2.5 equivalents of N-tert-butylhydroxylammonium acetate (III) are used per equivalent of aldehyde (II).

4. A process according to claim 1 in which the reaction solvent comprises an alcohol.

5. A process according to claim 1 in which the reaction solvent comprises a mixture of alcohols.

6. A process according to claim 4 in which the alcohol is methanol.

7. A process according to claim 4 in which the reaction solvent contains up to 10% by volume of water.

8. A process according to claim 7 in which the reaction solvent contains about 5% by volume of water.

9. A process according to claim 1 in which the product is isolated by crystallisation, characterised in that crystallisation is achieved by the addition of isopropanol to the reaction mixture.

10. A process according to claim 9 wherein 1.6 to 2.0 equivalents of N-tert-butylhydroxylammonium acetate (III) are used per equivalent of aldehyde (II).

* * * * *